United States Patent
Braun

(10) Patent No.: US 9,334,209 B2
(45) Date of Patent: May 10, 2016

(54) METHOD FOR HEAT RECOVERY IN VINYL CHLORIDE MONOMER STRUCTURES OR IN THE STRUCTURE COMPOSITE DICHLOROETHANE/VINYL CHLORIDE, AND DEVICE SUITABLE FOR SAME

(71) Applicants: THYSSENKRUPP INDUSTRIAL SOLUTIONS AG, Dortmund (DE); VINNOLIT GMBH & CO. KG, Burgkirchen (DE)

(72) Inventor: Manuel Braun, Gossersweiler (DE)

(73) Assignees: THYSSENKRUPP INDUSTRIAL SOLUTIONS AG, Essen (DE); VINNOLIT GMBH & CO. KG, Burgkirchen (DE)

( * ) Notice: Subject to any disclaimer, the term of this patent is extended or adjusted under 35 U.S.C. 154(b) by 0 days.

(21) Appl. No.: 14/760,002

(22) PCT Filed: Dec. 20, 2013

(86) PCT No.: PCT/EP2013/003878
§ 371 (c)(1),
(2) Date: Jul. 9, 2015

(87) PCT Pub. No.: WO2014/108159
PCT Pub. Date: Jul. 17, 2014

(65) Prior Publication Data
US 2015/0353452 A1 Dec. 10, 2015

(30) Foreign Application Priority Data
Jan. 10, 2013 (DE) .......................... 10 2013 000 325

(51) Int. Cl.
| | |
|---|---|
| *C07C 17/25* | (2006.01) |
| *C07C 17/395* | (2006.01) |
| *B01J 19/24* | (2006.01) |
| *C07C 17/383* | (2006.01) |
| *C01B 7/07* | (2006.01) |
| *B01D 3/00* | (2006.01) |

(52) U.S. Cl.
CPC ............. *C07C 17/395* (2013.01); *B01J 19/245* (2013.01); *C01B 7/0706* (2013.01); *C07C 17/25* (2013.01); *C07C 17/383* (2013.01); *B01D 3/007* (2013.01); *B01J 2219/0004* (2013.01); *B01J 2219/00074* (2013.01); *B01J 2219/24* (2013.01); *Y02P 20/51* (2015.11); *Y02P 70/34* (2015.11)

(58) Field of Classification Search
CPC ............................... C07C 17/25; C07C 17/395
USPC .................................... 570/226, 238
See application file for complete search history.

(56) References Cited

U.S. PATENT DOCUMENTS 4,747,914 A * 5/1988 Schwarzmaier ........ C07C 17/38
203/22
4,822,932 A * 4/1989 Dummer ................. C07C 17/25
570/226

* cited by examiner

*Primary Examiner* — Elvis O Price
(74) *Attorney, Agent, or Firm* — Brooks Kushman P.C.

(57) ABSTRACT

Energy savings in an integrated DCE/VCM plant, optionally also containing a PVC plant, is accomplished by using at least part of the vapor from a DEC quenching column to supply heat to an HCl column. The DCE plant has a high boiler column operating at superatmospheric pressure, and heat is removed from an overhead stream and used to supply heat to other portions of the process.

7 Claims, No Drawings

METHOD FOR HEAT RECOVERY IN VINYL CHLORIDE MONOMER STRUCTURES OR IN THE STRUCTURE COMPOSITE DICHLOROETHANE/VINYL CHLORIDE, AND DEVICE SUITABLE FOR SAME

CROSS REFERENCE TO RELATED APPLICATIONS

This application is the U.S. National Phase of PCT Appln. No. PCT/EP2013/003878 filed Dec. 20, 2013, which claims priority to German Application No. 10 2013 000 325.3 filed Jan. 10, 2013, the disclosures of which are incorporated in their entirety by reference herein.

BACKGROUND OF THE INVENTION

1. Field of the Invention

The invention relates to a process and an apparatus for preparing vinyl chloride monomer (hereinafter "VCM") and pertains to operating a column for separating off hydrogen chloride from the mixture obtained in the thermal dissociation of 1,2-dichloroethane (hereinafter "DCE"). Specifically, the invention pertains to heating the HCl column in the VCM plant or in an integrated plant for preparing both DCE and VCM.

The invention is directed to a process for preparing VCM which is usually obtained by thermal decomposition of DCE and from which polyvinyl chloride (hereinafter "PVC") is ultimately produced. The conversion of DCE into VCM forms hydrogen chloride (hereinafter "HCl"). DCE is therefore preferably prepared from ethylene and chlorine in such a way that a balance in respect of the hydrogen chloride produced and consumed in the reactions, as per the following reaction equations, is achieved:

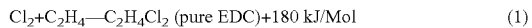
$$Cl_2 + C_2H_4 \rightarrow C_2H_4Cl_2 \text{ (pure EDC)} + 180 \text{ kJ/Mol} \quad (1)$$

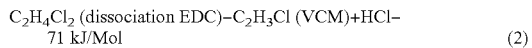
$$C_2H_4Cl_2 \text{ (dissociation EDC)} \rightarrow C_2H_3Cl \text{ (VCM)} + HCl - 71 \text{ kJ/Mol} \quad (2)$$

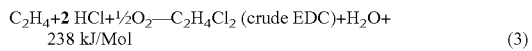
$$C_2H_4 + 2 \text{ HCl} + \tfrac{1}{2}O_2 \rightarrow C_2H_4Cl_2 \text{ (crude EDC)} + H_2O + 238 \text{ kJ/Mol} \quad (3)$$

2. Description of the Related Art

In processes for preparing vinyl chloride by incomplete dissociation of DCE, the DCE used is usually vaporized in the first step, the vapor formed is then pyrolytically dissociated at relatively high temperature in a second step, the entrained solids are then, in a third step, separated from the hot dissociation gas produced in the second step and the purified dissociation gas is subsequently fed to work-up by distillation.

HCl and VCM are formed as main products in the dissociation of DCE carried out in the second process step.

As by-products, traces of soot, chlorinated and unsaturated hydrocarbons and also benzene are obtained.

To limit the formation of these undesirable by-products, the temperature in the dissociation is kept at a level which leads to incomplete conversion of the DCE. The hot dissociation gas produced by dissociation in the second process step therefore still contains unreacted DCE in addition to the main products HCl and VCM and the abovementioned by-products.

The dissociation of EDC to form VCM is an endothermic process, and occurs in the gas phase in the form of pyrolysis. The pyrolysis is carried out industrially in the absence of a catalyst under a high pressure of from 1 to 3 MPa and at a temperature of from 450 to 600° C. However, catalytic processes which allow the pyrolysis to be carried out at lower temperature are also known.

The hot dissociation gas produced by means of pyrolysis is obtained at the pyrolysis temperature. It is conditioned so that it assumes a form suitable for the actual separation of materials. For this purpose, it is quenched in a quenching column, in which solids present in the dissociation gas are also scrubbed out. The solids are taken off at the bottom of the quenching column. The major part of the gaseous mixture of DCE, VCM and HCl (referred to as quenching vapor or quenching top vapor) is taken off at the top of the quenching column and passed to further work-up. Before the further work-up, the heat content of the quenching vapor can be utilized economically in one or more heat exchangers.

A plant complex for the production of vinyl chloride (hereinafter referred to as "VCM complex") consists essentially of:
- a plant for preparing DCE from ethene and chlorine ("direct chlorination", optional plant component); and
- a plant for preparing DCE from ethene, hydrogen chloride and oxygen ("oxychlorination"); and
- a plant for purifying 1,2-dichloroethane by distillation (preparation of "feed DCE"); and
- a plant for the thermal dissociation of the "feed DCE" which has been purified by distillation into vinyl chloride and hydrogen chloride; and
- a plant for separating off the hydrogen chloride and unreacted 1,2-dichloroethane by distillation and also for purifying the vinyl chloride.

The hydrogen chloride obtained by thermal dissociation of 1,2-dichloroethane is recirculated to the oxychlorination plant and once again reacted there with ethene and oxygen to form DCE.

Numerous measures for saving energy or recovering heat in plants for the preparation of DCE, VCM and PVC are known from the prior art. Such measures lead to a significant decrease in the operating costs and thus contribute quite substantially to the economics of the plant. Likewise, such measures also contribute significantly to reducing the $CO_2$ emissions from the plant.

These include measures which utilize the heat of reaction of the exothermic reaction steps in order to heat heat sinks in the process. Thus, for example, the heat of reaction from the oxychlorination is used to produce steam by means of which, for example, feed preheaters or distillation columns can be heated.

There have likewise been proposals for utilizing heat energy originating from the VCM plant. An example of such processes may be found in DE 34 40 685 A1. Here, the vapor from the high-boiler column is mechanically compressed and used for heating the same column. The DCE obtained in the circulating convection vaporizer of the high-boiler column by condensation of the mechanically compressed vapor is then used as feed DCE in the thermal dissociation after it has been preheated further by the flue gases from the dissociation oven. In another process variant described in WO 2004/089860 A1, the vapor from the quenching column downstream of the dissociation oven is utilized for preheating the feed DCE.

DE 31 47 310 A1 discloses a method of recovering heat in the preparation of VCM by dissociation of DCE. Here, heat is recovered from dissociation gases produced in the preparation of VCM and used for heating distillation columns. The dissociation of DCE is carried out under superatmospheric pressure and the dissociation gases are quenched by direct cooling. In an example, the thermal energy obtained is used for operating distillation columns downstream of the quenching column.

DE 29 13 004 A describes a method of recovering pyrolysis energy in the preparation of vinyl chloride by incomplete thermal dissociation of 1,2-dichloroethane. In this document, it is proposed that steam be generated in a heat exchanger by means of the heat content of the hot dissociation gases from the dissociation oven and this steam then be used for heating columns.

DE 35 19 161 A1 discloses a process for purifying 1,2-dichloroethane. Here, a distillation column is operated under superatmospheric pressure and the heat content of the overhead stream is used for heating further heat sinks. The dichloroethane obtained is so hot that is used for heating 1,2-dichloroethane-comprising product streams.

Recently, plant concepts in which the DCE column is operated in the mode of "pressure distillation" have been proposed. A consequence of this is that the feed DCE (for the thermal dissociation to form VCM) obtained in this process has a considerably increased temperature compared to earlier processes. This removes the necessity of preheating this feed DCE before the dissociation, or preheating requires considerably less heat energy than in the case of earlier processes. Hitherto, the feed DCE was heated mainly by the heat content of the dissociation quenching vapor. This heat source could now be passed to other uses or the dissociation quenching vapor would have to be cooled in another way, for example in an air-cooled condenser.

SUMMARY OF THE INVENTION

It is an object of the present invention to provide a process for preparing VCM by thermal dissociation of DCE, which is extremely energy-efficient and does not require any great modification of existing plants or plant components. It has now surprisingly been found that the dissociation quenching vapor can be used in a particularly economical way for heating the HCl column in VCM plants having preceding DCE plants in which high-boiler columns operated under superatmospheric pressure are used.

DETAILED DESCRIPTION OF THE PREFERRED EMBODIMENTS

The present invention thus provides a process for preparing vinyl chloride by thermal dissociation of 1,2-dichloroethane in a vinyl chloride plant provided with a 1,2-dichloroethane pyrolysis unit in which the feed 1,2-dichloroethane is thermally dissociated, the dissociation gas produced therein is cooled in a downstream quenching column and the hydrogen chloride present in the dissociation gas is separated off in a downstream HCl column, where the vinyl chloride plant is preceded by a 1,2-dichloroethane plant which has a purification of 1,2-dichloroethane by distillation, which is provided with at least one high-boiler column in which substances having boiling points higher than that of 1,2-dichloroethane are separated off, where the high-boiler column is operated under superatmospheric pressure, preferably under a superatmospheric pressure in the range from 2.7 to 5.3 bar. The process of the invention is characterized in that at least part of the vapor from the quenching column is used for the recovery of thermal energy which is utilized for heating the HCl column.

Owing to the relatively high temperature level of the dissociation quenching vapor, utilization for heating the HCl column is possible.

The high-boiler column is most preferably operated at temperatures at the high end of the range of 120-150° C., and at least part of the overhead stream from the high-boiler column is used for recovering thermal energy which is utilized in heat sinks of a subplant for preparing and purifying 1,2-dichloroethane and/or in heat sinks of a downstream subplant for preparing and purifying vinyl chloride and/or in heat sinks of a downstream subplant for preparing and working up polyvinyl chloride.

In a particularly preferred variant of the process of the invention, the thermal energy obtained from the overhead stream from the quenching column is not used for heating the feed 1,2-dichloroethane for the 1,2-dichloroethane pyrolysis unit.

According to the invention, heating of the HCl column is effected using this thermal energy, with preference being given to at least 50%, more preferably at least 70%, of the thermal energy originating from vapor from the quenching column and the remainder coming from low-pressure steam.

The invention also provides an apparatus for preparing vinyl chloride by thermal dissociation of 1,2-dichloroethane in a vinyl chloride plant, which comprises the elements:
A) a 1,2-dichloroethane pyrolysis unit in which the feed 1,2-dichloroethane is thermally dissociated,
B) a quenching column which is located downstream of the 1,2-dichloroethane pyrolysis unit and in which the dissociation gas produced is cooled and solids are scrubbed out,
C) an HCl column which is located downstream of the quenching column and in which the hydrogen chloride present in the dissociation gas is separated off, and
D) at least one heat exchanger in which thermal energy utilized for heating the HCl column is recovered from at least part of the vapor from the quenching column,
E) a plant for preparing and purifying 1,2-dichloroethane which is located upstream of the vinyl chloride plant and has a purification by distillation of 1,2-dichloroethane and is
F) provided with at least one high-boiler column in which substances having boiling points higher than that of 1,2-dichloroethane are separated off, with the high-boiler column being designed so that it can be operated under superatmospheric pressure.

In a preferred variant of the apparatus of the invention, at least one heat exchanger which is heated by means of vapor from the high-boiler column and in which the thermal energy recovered is used for heating heat sinks in the 1,2-dichloroethane plant and/or heat sinks in the vinyl chloride plant and/or heat sinks in a polyvinyl chloride subplant located downstream of the vinyl chloride plant is provided.

Suitable and preferred heat sinks in a plant complex for DCE/VCM/PVC production are:
In the DCE complex:
dewatering column;
low-boiler column or DCE stripper;
vacuum column;
boiler feed water degasser; and
stripping column for removing DCE from wastewater.
In the VCM complex:
stripping column for purification (removal of HCl) of vinyl chloride.
In the PVC plant:
apparatuses for removing residual monomer (VCM) from PVC, specifically a predegassing device and a downstream degassing column;
stripping column for removing VCM from wastewater;
apparatus for drying PVC powder; and apparatus for heating feed water for the polymerization reaction.

The following example illustrates the invention without limiting it.

EXAMPLE

One or more heat exchangers in which the vapor from the quenching column is cooled were installed between dissociation quench and HCl column and the recovered heat content was used for heating the HCl column. Heating of the HCl column is carried out according to the following scenario:
- 90% of the heat required was provided by the vapor-heated reboiler and
- 10% of the heat required was provided by low-pressure steam via a trim reboiler.

In a specific case, utilization of 4533 kW of latent heat from the dissociation quenching vapor enabled 7825 kg/h of low-pressure steam to be saved at an annual production of 400,000 tonnes of VCM over 8000 h.

The feed DCE for the dissociation quench originated from a DCE plant having a high-boiler column which was operated under superatmospheric pressure. The temperatures at the top were in the range from 120 to 150° C.

The invention claimed is:

1. A process for preparing vinyl chloride by thermal dissociation of 1,2-dichloroethane in a vinyl chloride plant, comprising:
   thermally dissociating 1,2-dichloroethane in a 1,2-dichloroethane pyrolysis unit;
   cooling the dissociation gas produced thereby in a downstream quenching column and separating hydrogen chloride present in the dissociation gas in a downstream HCl column,
   wherein the vinyl chloride plant is preceded by a 1,2-dichloroethane plant in which 1,2-dichloroethane is purified by distillation, and which is provided with at least one high-boiler column operated under superatmospheric pressure for separating substances having boiling points higher than that of 1,2-dichloroethane, the process further comprising recovering thermal energy from at least part of a vapor from the quenching column and heating the HCl column with the recovered thermal energy.

2. The process of claim 1, wherein the high-boiler column is operated under a superatmospheric pressure in the range from 2.7 to 5.3 bar.

3. The process of claim 2, wherein the high-boiler column is operated at temperatures in the range of 120-150° C. and at least part of an overhead stream from the high-boiler column is used for recovering thermal energy which is utilized in one or more heat sink(s) of a subplant for preparing 1,2-dichloroethane, heat sink(s) of a downstream subplant for producing vinyl chloride, and/or heat sink(s) of a downstream subplant for preparing polyvinyl chloride.

4. The process of claim 1, wherein heating of the HCl column is effected by means of thermal energy which originates to an extent of at least 50% from vapor from the quenching column, the remainder provided by low-pressure steam.

5. The process of claim 1, wherein heating of the HCl column is effected by means of thermal energy which originates to an extent of at least 70% from vapor from the quenching column, the remainder provided by low-pressure steam.

6. An apparatus for preparing vinyl chloride by thermal dissociation of 1,2-dichloroethane in a vinyl chloride plant, comprising the elements:
   A) a 1,2-dichloroethane pyrolysis unit in which a 1,2-dichloroethane feed is thermally dissociated,
   B) a quenching column located downstream from the 1,2-dichloroethane pyrolysis unit in which dissociation gas produced by pyrolysis is cooled and solids are scrubbed out,
   C) an HCl column located downstream from the quenching column in which hydrogen chloride present in the dissociation gas is separated,
   D) at least one heat exchanger in which thermal energy utilized for heating the HCl column is recovered from at least part of vapor from the quenching column,
   E) a plant for preparing and purifying 1,2-dichloroethane which is located upstream of the vinyl chloride plant and has a 1,2-dichloroethane purifying distillation vessel and is
   F) provided with at least one high-boiler column in which substances having boiling points higher than that of 1,2-dichloroethane are separated off, the high-boiler column being configured to operate at superatmospheric pressure.

7. The apparatus of claim 6, further comprising at least one heat exchanger which is heated by vapor from the high-boiler column, wherein thermal energy recovered by the heat exchanger is used for heating heat sink(s) in the 1,2-dichloroethane plant, heat sink(s) in the vinyl chloride plant, and/or heat sink(s) in a polyvinyl chloride subplant located downstream of the vinyl chloride plant.

* * * * *